US012721523B2

(12) United States Patent
Forneris et al.

(10) Patent No.: US 12,721,523 B2
(45) Date of Patent: Sep. 1, 2026

(54) METHOD OF AND SYSTEM FOR IN VIVO STRAIN MAPPING OF AN AORTIC DISSECTION

(71) Applicant: VITAA MEDICAL SOLUTIONS INC., Montréal (CA)

(72) Inventors: Arianna Forneris, Edmonton (CA); Elena Di Martino, Calgary (CA); Randy D. Moore, Chestermere (CA)

(73) Assignee: VITAA MEDICAL SOLUTIONS INC., Montreal (CA)

( * ) Notice: Subject to any disclaimer, the term of this patent is extended or adjusted under 35 U.S.C. 154(b) by 551 days.

(21) Appl. No.: 18/034,719

(22) PCT Filed: Feb. 3, 2022

(86) PCT No.: PCT/IB2022/050931
§ 371 (c)(1),
(2) Date: May 1, 2023

(87) PCT Pub. No.: WO2022/167959
PCT Pub. Date: Aug. 11, 2022

(65) Prior Publication Data

US 2023/0397816 A1 Dec. 14, 2023

Related U.S. Application Data

(60) Provisional application No. 63/145,205, filed on Feb. 3, 2021.

(51) Int. Cl.
*A61B 5/00* (2006.01)
*A61B 5/02* (2006.01)
(Continued)

(52) U.S. Cl.
CPC .......... *A61B 5/004* (2013.01); *A61B 5/02014* (2013.01); *A61B 5/1075* (2013.01);
(Continued)

(58) Field of Classification Search
CPC ..... A61B 5/004; A61B 5/02014; A61B 5/055; A61B 5/1075; A61B 5/352; A61B 5/7275;
(Continued)

(56) References Cited

U.S. PATENT DOCUMENTS

2015/0196250 A1 7/2015 Nair
2020/0118688 A1 4/2020 Pasta et al.

FOREIGN PATENT DOCUMENTS

CN 105580019 A * 5/2016 ............. G16H 50/50
JP 2013-183875 A 9/2013
(Continued)

OTHER PUBLICATIONS

Extended European Search Report; European Patent Office; European Application No. 22749330.1; Nov. 13, 2024; 8 pages.
(Continued)

*Primary Examiner* — Matthew C Bella
(74) *Attorney, Agent, or Firm* — Taft Stettinius & Hollister LLP

(57) ABSTRACT

A method and a system for generating a strain map of a dissected blood vessel. A multiphase stack of the dissected blood vessel is received, with a given phase of the multiphase stack representing the blood vessel at a given time in a cardiac cycle. A 3D geometrical model of the blood vessel includes a wall of the blood vessel and a dissection flap is generated. A surface mesh of the blood vessel for a first phase is generated, the surface mesh including a blood vessel wall surface mesh and a dissection flap surface mesh. A local deformation at each phase is determined by mapping voxels of the surface mesh of the blood vessel to the multiphase stack. A strain map including principal strain
(Continued)

values is generated using the local deformation and the blood vessel wall surface mesh and the dissection flap surface mesh.

20 Claims, 6 Drawing Sheets

(51) Int. Cl.

| | |
|---|---|
| ***A61B 5/107*** | (2006.01) |
| ***A61B 5/352*** | (2021.01) |
| ***G06T 7/00*** | (2017.01) |
| ***G06T 7/246*** | (2017.01) |
| ***G06T 17/00*** | (2006.01) |
| ***G06T 19/20*** | (2011.01) |
| ***G16H 30/40*** | (2018.01) |
| ***G16H 50/20*** | (2018.01) |
| ***G16H 50/50*** | (2018.01) |
| *A61B 5/055* | (2006.01) |

(52) U.S. Cl.

CPC ............ *A61B 5/352* (2021.01); *A61B 5/7275* (2013.01); *G06T 7/0012* (2013.01); *G06T 7/251* (2017.01); *G06T 17/00* (2013.01); *G06T 19/20* (2013.01); *G16H 30/40* (2018.01); *G16H 50/20* (2018.01); *G16H 50/50* (2018.01); *A61B 5/055* (2013.01); *A61B 2576/02* (2013.01); *G06T 2207/10076* (2013.01); *G06T 2207/10081* (2013.01); *G06T 2207/10088* (2013.01); *G06T 2207/30101* (2013.01); *G06T 2210/41* (2013.01)

(58) Field of Classification Search

CPC ... A61B 2576/02; G06T 7/0012; G06T 7/251; G06T 17/00; G06T 19/20; G06T 2207/10076; G06T 2207/10081; G06T 2207/10088; G06T 2207/30101; G06T 2210/41; G06T 7/11; G06T 7/50; G06T 2207/10136; G06T 2219/2012; G16H 30/40; G16H 50/20; G16H 50/50

See application file for complete search history.

(56) References Cited

FOREIGN PATENT DOCUMENTS

| | | | | | |
|---|---|---|---|---|---|
| JP | 2013-534154 A | | 9/2013 | | |
| JP | 2014-100249 A | | 6/2014 | | |
| JP | 2018-110804 A | | 7/2018 | | |
| KR | 1020160136499 A | | 11/2016 | | |
| KR | 20210072952 A | * | 6/2021 | ............. | A61B 6/481 |
| WO | 2009081598 A1 | | 7/2009 | | |
| WO | 2018068153 A1 | | 4/2018 | | |

OTHER PUBLICATIONS

Tamas Kovacs et al.; Automatic Segmentation of the Aortic Dissection Membrane from 3D CTA Images; 8 pages; Medical Imaging and Augmented Reality Lecture Notes in Computer Science; Copyright Springer-Verlag Berlin Heidelberg; pp. 317-324; Jan. 1, 2006.

International Search Report; Canadian Intellectual Property Office; International Application No. PCT/IB2022/050931; Apr. 12, 2022; 4 pages.

Written Opinion of the International Searching Authority; Canadian Intellectual Property Office; International Application No. PCT/IB2022/050931; Apr. 12, 2022; 4 pages.

Tamas Kovacs et al.; Automatic Segmentation of the Aortic Dissection Membrane from 3D CTA Images; 2006; 8 pages; LNCS 4091; Copyright Springer-Verlag Berlin Heidelberg 2006.

JP Office Action; Japanese Patent Office; Japanese Patent Application No. 2023-539843; Feb. 3, 2026; 9 pages.

* cited by examiner

METHOD OF AND SYSTEM FOR IN VIVO STRAIN MAPPING OF AN AORTIC DISSECTION

CROSS REFERENCE TO RELATED APPLICATIONS

This application is a U.S. National Phase of International PCT Application No. PCT/IB2022/050931 filed Feb. 3, 2022, which claims priority to U.S. Provisional Patent Application No. 63/145,205 filed Feb. 3, 2021, the contents of each application are incorporated herein by reference in their entirety.

FIELD

The present technology pertains to the field of medical imaging. More specifically, the present technology relates to a method and a system for in vivo assessment of deformations in a dissected aorta based on electrocardiographically (ECG)-gated acquired images.

BACKGROUND

An aortic dissection (AD) originates from the delamination of the aortic wall and the formation of a tear in its innermost layer (intima layer). The initial tearing results in blood flowing between the intima and media causing further separation of these layers and the formation of a second lumen (false lumen), isolated from the true lumen by the remaining intima layer called, in this case, intimal flap or dissection flap. With reference to FIG. 1, there is shown a slice of a Digital Imaging and Communications in Medicine (DICOM) stack obtained from static computation tomography (CT) imaging showing the presence of a dissection in the descending portion of an aorta, where the arrow points to the dissection flap that separates the small "true" lumen from the larger "false" lumen.

Depending on the presence of secondary (or re-entry) tears, the AD can be characterized as a communicating or non-communicating dissection.

The development of an aortic dissection introduces critical changes in the arterial geometry and hemodynamics possibly leading to aortic rupture or malperfusion to vital organs due to compression and collapse of the true lumen by the pressurized false lumen. For this reason, AD carries high mortality rate (20% before reaching the hospital and ranging from 3%/hour in the first 24 hours to up to 90% at one year if untreated) [1] despite low incidence, and is associated with co-morbidities and long-term complications, such as aneurysmal degeneration, that is the dilatation of the false lumen.

Despite several risk factors associated with AD (such as age, hypertension, connective tissue disorder, deceleration trauma, bicuspid valve, previous cardiac surgery, vascular inflammation), the pathogenesis of this disease is not fully understood. Aortic aneurysm, intramural hematoma and penetrating atherosclerotic ulcer in the media have been identified as causes of aortic weakening and precursors of the initial tearing that can disrupt the intima and evolve into a dissection; however these are not the only causes of AD. For example, the case of aortic aneurysm evolving into a dissection is reported in only about 20% of acute dissections, suggesting a pre-existing degeneration of the media as a substrate for the pathology initiation and an overall different pathological pathway.

Given that the location of initial intimal tearing and the anatomical involvement of the dissection have been identified as pivotal in the disease progression, clinically recognized classifications of AD were introduced in order to help disease management based on anatomical features with respect to prognosis. On one hand, the Stanford classification system identifies type A and type B aortic dissections, with the first involving the ascending thoracic aorta, regardless of the tearing location, and the second originating beyond the left subclavian artery, therefore with no involvement of the ascending segment of the aorta. On the other hand, the DeBakey classification system refers to the site of initial intimal tearing, with DeBakey type I AD originating in the ascending aorta and propagating into the arch or beyond it, DeBakey type II AD originating in and being limited to the ascending aorta, and DeBakey type III AD originating in the descending aorta. These classifications allow for the identification of dissections that require surgical repair and those cases that can benefit from a less invasive medical treatment. The location of principal tearing and the overall anatomical involvement are, in fact, important factors in defining the optimal treatment. More proximal entry tears have been associated with poor clinical outcome and higher mortality, therefore dictating the need for a more invasive treatment and recommended intervention (such as open or endovascular repair) for type A ADs even when the patient does not present critical complications, such as malperfusion, or co-morbidities. Conversely, Type B ADs have been typically treated conservatively using beta blockers to control blood pressure unless a critical complication is present and needs to be addressed surgically.

The temporal evolution of a dissected aorta and the duration of symptoms are also important contributors to mortality therefore affecting clinical decisions. The acute phase of an AD is defined as the first two weeks since initial onset of symptoms of aortic tearing, while the following weeks represent the so called sub-acute phase (between two weeks and a month since initial onset) and chronic phase (beyond a month since onset). Patients with type A AD rarely reach a chronic phase as they are typically treated as urgent cases benefiting from intervention in the acute phase. The chronic phase is more common in patients with type B AD, and the sub-acute phase represents an important window to monitor for potential long-term complications of uncomplicated type B cases that are usually stable in the short-term.

Despite recognized clinical guidelines, the management of AD is still debated and controversial. A typical controversy regards the management of type B and residual type B aortic dissection in patients that received surgical repair of the ascending aorta but are left with a dissection in the descending portion of the artery.

Uncomplicated and residual type B dissections are, in fact, considered stable in the short term but can progress and develop complications such as aneurysm of the false lumen (20-40% within 1-5 years) with consequent increased risks for the patient. The management of these cases is controversial and there is little clinical consensus on whether early intervention could be beneficial for some patients to prevent long-term adverse outcomes. More recent literature findings and evidence suggest thoracic endovascular repair (TEVAR) should be considered in addition to pharmacological treatment in order to improve long-term outcomes and prevent late complications in suitable subjects. The endovascular option, although less invasive, is not free from risk as the insertion of a stent-graft can be problematic in an already compromised aortic anatomy with a weakened wall and could promote retrograde dissection or partial thrombosis.

Another factor in deciding how to manage ADs is the dynamic behaviour of the dissection flap exposed to the pulsatile blood flow as it may compromise the placement and durability of a stent-graft. While in the acute and sub-acute phases the dissection flap is subject to movement during the cardiac cycle, it becomes thicker and fibrotic, characterized by a stiffer behaviour as the disease progresses towards the chronic phase.

The TEVAR approach should usually be selected after an accurate evaluation of benefits versus treatment-related risks on a patient-specific basis. In this context, different studies reported on the false lumen patency and maximum aortic diameter (bigger than 40 mm) as risk factors for later aneurysm formation and adverse outcome. According to some findings it may be essential to accurately assess the size of the false lumen and the entry tear as a larger false lumen and a larger entry tear are likely to induce higher flow rate in the false lumen consequently promoting its patency.

The complex management of ADs stems from the anatomical complexity of dissected aortas and the strong dependence and interplay between geometry and hemodynamics affecting the mutual interaction of the two lumens. In this regard, the pressure difference between the true and false lumens can cause the compression and dynamic obstruction of the true lumen potentially leading to a flow reduction to organs downstream of the dissection, therefore increasing the risk for ischemic events. Moreover, a pressurized false lumen could favor enlargement and aneurysmal degeneration when large differences in pressure are generated between the two lumens and maintained over the cardiac cycle.

Another factor contributing to the long term-outcome of ADs is the thrombosis of the false lumen, often promoted by slow, stagnating flow: a complete false lumen thrombosis has been associated to higher survival rates while a partial thrombosis, that may cause occlusion of distal tears impeding blood re-entry and leading to increased pressure, has been linked to adverse outcomes and increased mortality.

Imaging modalities such as CT, 3D or 4D MRI, provide anatomical information along with blood fluid dynamics information that can help the clinical assessment of a dissected aorta but do not provide non-invasive pressure measurements in the false lumen and dissected region. Current standard of care relies on the use of contrast-enhanced CT imaging for the identification and assessment of aortas subject to dissection.

Therefore, there is a need for improving the assessment of the severity of a dissected blood vessel.

SUMMARY

It is an object of the present technology to ameliorate at least some of the inconveniences present in the prior art. One or more embodiments of the present technology may provide and/or broaden the scope of approaches to and/or methods of achieving the aims and objects of the present technology.

One or more embodiments of the present technology have been developed based on developers' appreciation that there is a clinical need to improve the management of ADs with methods and systems that can complement standard medical imaging techniques and provide an objective assessment of the severity of the dissection, a measure of the weakening of the aortic wall with respect to non-dissected regions and an evaluation of the dynamic behaviour and interaction of the dissection flap, true lumen and false lumen with the potential to help risk stratification and support decision-making for treatment options on a case-by-case basis.

More specifically, based on the above, developers of the present technology have appreciated that ADs are complex to model and simulate by using computational fluid dynamics (CFD) and fluid-structure-interaction (FSI) simulation techniques, which generally require assumptions of homogenous material properties, which may not apply in the case of ADs, as the tissues of different portions of a dissected aorta have different material properties and there is often absence of blood flow in a false lumen of a dissected blood vessel.

The present technology enables obtaining a substantially objective assessment of aortic dissections compared to current standard of care by providing information accessible only through analysis using methods and system described herein and will complement the anatomical assessment based on medical images. The present technology may be used to support outcome prediction for risk stratification and treatment selection purposes on a patient-specific basis, thus changing patient care standards in the field of aortic dissections.

Thus, one or more embodiments of the present technology are directed to a method of and a system for in vivo strain mapping of an aortic dissection.

In accordance with a broad aspect of the present technology, there is provided a method for generating a strain map of a dissected blood vessel of a given subject. The method is executed by a processor, the method comprises: receiving a multiphase stack having been generated from a plurality of images of the dissected blood vessel of the given subject, a given phase of the multiphase stack is representative of the dissected blood vessel at a given time in a cardiac cycle, generating, using at least a portion of the multiphase stack, a 3D geometrical model of at least a portion of the dissected blood vessel, the 3D geometrical model comprises a wall of the dissected blood vessel and a dissection flap. The method comprises generating, using the 3D geometrical model, a surface mesh of at least the portion of the dissected blood vessel for a first phase of the multiphase stack, the surface mesh of at least the portion of the dissected blood vessel comprises a blood vessel wall surface mesh and a dissection flap surface mesh, determining, using the surface mesh of at least the portion of the dissected blood vessel and the multiphase stack, a local deformation at each phase of the multiphase stack by mapping voxels of the surface mesh of the dissected blood vessel to the multiphase stack at each of the phases. The method comprises generating, using the local deformation at each phase and the blood vessel wall surface mesh and the dissection flap surface mesh, a set of strain maps, a given strain map of the set of strain maps comprising principal strain values at the surface of the dissected blood vessel for a corresponding phase of the cardiac cycle, and outputting the set of strain maps.

In one or more embodiments of the method, the method further comprises: generating, using the set of strain maps, a maximum strain map indicative of maximum principal strain values over the cardiac cycle, and outputting the maximum strain map.

In one or more embodiments of the method, the method further comprises: generating, using the 3D geometrical model and the set of strain maps, an interactive model of the dissected blood vessel, and transmitting, for display on a display interface connected to the processor, the interactive model of the dissected blood vessel.

In one or more embodiments of the method, said generating the set of strain maps comprises, for the given strain map, projecting strain in principal directions of curvature to obtain a circumferential strain value and an axial strain value on the surface mesh of the dissected blood vessel.

In one or more embodiments of the method, said generating using the multiphase stack, the 3D geometrical model of at least the portion of the dissected blood vessel comprises: segmenting the multiphase stack to obtain a segmented dissected blood vessel and using the segmented dissected blood vessel to obtain the 3D geometrical model.

In one or more embodiments of the method, the method further comprises, prior to said receiving of the multiphase stack having been generated from the plurality of images: receiving the plurality of images, the plurality of images having been acquired using an electrocardiographically (ECG)-gated medical imaging apparatus, and generating, using the plurality of images, the multiphase stack.

In one or more embodiments of the method, said generating the surface mesh comprises smoothing the 3D geometrical model to obtain the surface mesh of the dissected blood vessel.

In one or more embodiments of the method, said determining, using the surface mesh and the multiphase stack, the local deformation at each phase of the multiphase stack by mapping voxels of the surface mesh to the multiphase stack comprises using an optical flow algorithm.

In one or more embodiments of the method, the 3D geometrical model of at least the portion of the dissected blood vessel comprises an indication of a true lumen and a false lumen.

In one or more embodiments of the method, the method further comprises: assessing, using the set of strain maps of the dissected blood vessel, a mobility of the dissection flap, and identifying pressurization of the false lumen and compression of the true lumen over the cardiac cycle.

In one or more embodiments of the method, the 3D geometrical model of at least a portion of the dissected blood vessel further comprises an indication of a healthy non-dissected region of the blood vessel.

In one or more embodiments of the method, the method further comprises: determining, using the set of strain maps of the dissected blood vessel over the cardiac cycle and the indication of the healthy non-dissected region, a regional weakening in the dissected blood vessel.

In one or more embodiments of the method, the method further comprises: predicting, using the set of strain maps of the dissection flap, an enlargement of a dissection tear in the dissected blood vessel.

In one or more embodiments of the method, the method further comprises: repeating said method for a second multiphase stack of the dissected blood vessel of the given subject having been acquired at a subsequent time to thereby obtain a further 3D geometrical model of the dissected blood vessel and a further set of strain maps for the subsequent time.

In one or more embodiments of the method, the method further comprises: generating, using the 3D geometrical model, the set of strain maps, the further 3D geometrical model and the further strain map at each phase of the cardiac cycle, a further interactive model comprises a geometrical and strain evolution of the dissected blood vessel.

In one or more embodiments of the method, the method further comprises: predicting, using the set of strain maps and the further set of strain maps, a further regional weakening in the dissected blood vessel.

In one or more embodiments of the method, the method further comprises: predicting, using the set of strain maps and the further set of strain maps, a further enlargement of a dissection tear in the dissected blood vessel.

In accordance with a broad aspect of the present technology, there is provided a system comprises: a processor, and a non-transitory storage medium operatively connected to the processor. The non-transitory storage medium comprises computer-readable instructions stored thereon, the processor, upon executing the computer-readable instructions, is configured for: receiving a multiphase stack having been generated from a plurality of images of the dissected blood vessel of the given subject, a given phase of the multiphase stack is representative of the dissected blood vessel at a given time in a cardiac cycle, generating, using at least a portion of the multiphase stack, a 3D geometrical model of at least a portion of the dissected blood vessel, the 3D geometrical model comprises a wall of the dissected blood vessel and a dissection flap. The processor is configured for generating, using the 3D geometrical model, a surface mesh of at least the portion of the dissected blood vessel for a first phase of the multiphase stack, the surface mesh of at least the portion of the dissected blood vessel comprises a blood vessel wall surface mesh and a dissection flap surface mesh, determining, using the surface mesh of at least the portion of the dissected blood vessel and the multiphase stack, a local deformation at each phase of the multiphase stack by mapping voxels of the surface mesh of the dissected blood vessel to the multiphase stack at each of the phases, generating, using the local deformation at each phase and the blood vessel wall surface mesh and the dissection flap surface mesh, a set of strain maps, a given strain map of the set of strain maps comprising principal strain values at the surface of the dissected blood vessel for a corresponding phase of the cardiac cycle, and outputting the set of strain maps.

In one or more embodiments of the system, the processor is further configured for: generating, using the set of strain maps, a maximum strain map indicative of maximum principal strain values over the cardiac cycle, and outputting the maximum strain map.

In one or more embodiments of the system, the processor is further configured for: generating, using the 3D geometrical model and the set of strain maps, an interactive model of the dissected blood vessel, and transmitting, for display on a display interface connected to the processor, the interactive model of the dissected blood vessel.

In one or more embodiments of the system, said generating the set of strain maps comprises, for the given strain map, projecting strain in principal directions of curvature to obtain a circumferential strain value and an axial strain value on the surface mesh of the dissected blood vessel.

In one or more embodiments of the system, said generating using the multiphase stack, the 3D geometrical model of at least the portion of the dissected blood vessel comprises: segmenting the multiphase stack to obtain a segmented dissected blood vessel and using the segmented dissected blood vessel to obtain the 3D geometrical model.

In one or more embodiments of the system, the processor is further configured for, prior to said receiving of the multiphase stack having been generated from the plurality of images: receiving the plurality of images, the plurality of images having been acquired using an electrocardiographically (ECG)-gated medical imaging apparatus, and generating, using the plurality of images, the multiphase stack.

In one or more embodiments of the system, said generating the surface mesh comprises smoothing the 3D geometrical model to obtain the surface mesh of the dissected blood vessel.

In one or more embodiments of the system, said determining, using the surface mesh and the multiphase stack, the local deformation at each phase of the multiphase stack by mapping voxels of the surface mesh to the multiphase stack comprises using an optical flow algorithm.

In one or more embodiments of the system, the 3D geometrical model of at least the portion of the dissected blood vessel comprises an indication of a true lumen and a false lumen.

In one or more embodiments of the system, the processor is further configured for: assessing, using the set of strain maps of the dissected blood vessel, a mobility of the dissection flap, and identifying pressurization of the false lumen and compression of the true lumen over the cardiac cycle.

In one or more embodiments of the system, the 3D geometrical model of at least a portion of the dissected blood vessel further comprises an indication of a healthy non-dissected region of the blood vessel.

In one or more embodiments of the system, the processor is further configured for: determining, using the set of strain maps of the dissected blood vessel over the cardiac cycle and the indication of the healthy non-dissected region, a regional weakening in the dissected blood vessel.

In one or more embodiments of the system, the processor is further configured for: predicting, using the strain map of the dissection flap, an enlargement of a dissection tear in the dissected blood vessel.

In one or more embodiments of the system, the processor is further configured for executing the computer-readable instructions for a second multiphase stack of the dissected blood vessel of the given subject having been acquired at a subsequent time to thereby obtain a further 3D geometrical model of the dissected blood vessel and a further set of strain maps for the subsequent time.

In one or more embodiments of the system, the processor is further configured for: generating, using the 3D geometrical model, the set of strain maps, the further 3D geometrical model and the further strain map at each phase of the cardiac cycle, a further interactive model comprises a geometrical and strain evolution of the dissected blood vessel.

In one or more embodiments of the system, the processor is further configured for: predicting, using the set of strain maps and the further set of strain maps, a further regional weakening in the dissected blood vessel.

In one or more embodiments of the system, the processor is further configured for: predicting, using the set of strain maps and the further set of strain maps, a further enlargement of a dissection tear in the dissected blood vessel.

Definitions

In the context of the present specification, a "server" is a computer program that is running on appropriate hardware and is capable of receiving requests (e.g., from electronic devices) over a network (e.g., a communication network), and carrying out those requests, or causing those requests to be carried out. The hardware may be one physical computer or one physical computer system, but neither is required to be the case with respect to the present technology. In the present context, the use of the expression "a server" is not intended to mean that every task (e.g., received instructions or requests) or any particular task will have been received, carried out, or caused to be carried out, by the same server (i.e., the same software and/or hardware); it is intended to mean that any number of software elements or hardware devices may be involved in receiving/sending, carrying out or causing to be carried out any task or request, or the consequences of any task or request; and all of this software and hardware may be one server or multiple servers, both of which are included within the expressions "at least one server" and "a server".

In the context of the present specification, "electronic device" is any computing apparatus or computer hardware that is capable of running software appropriate to the relevant task at hand. Thus, some (non-limiting) examples of electronic devices include general purpose personal computers (desktops, laptops, netbooks, etc.), mobile computing devices, smartphones, and tablets, and network equipment such as routers, switches, and gateways. It should be noted that an electronic device in the present context is not precluded from acting as a server to other electronic devices. The use of the expression "an electronic device" does not preclude multiple electronic devices being used in receiving/sending, carrying out or causing to be carried out any task or request, or the consequences of any task or request, or steps of any method described herein. In the context of the present specification, a "client device" refers to any of a range of end-user client electronic devices, associated with a user, such as personal computers, tablets, smartphones, and the like.

In the context of the present specification, the expression "computer readable storage medium" (also referred to as "storage medium" and "storage") is intended to include non-transitory media of any nature and kind whatsoever, including without limitation RAM, ROM, disks (CD-ROMs, DVDs, floppy disks, hard drivers, etc.), USB keys, solid state-drives, tape drives, etc. A plurality of components may be combined to form the computer information storage media, including two or more media components of a same type and/or two or more media components of different types.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus, information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, unless expressly provided otherwise, an "indication" of an information element may be the information element itself or a pointer, reference, link, or other indirect mechanism enabling the recipient of the indication to locate a network, memory, database, or other computer-readable medium location from which the information element may be retrieved. For example, an indication of a document could include the document itself (i.e., its contents), or it could be a unique document descriptor identifying a file with respect to a particular file system, or some other means of directing the recipient of the indication to a network location, memory address, database table, or other location where the file may be accessed. As one skilled in the art would recognize, the degree of precision required in such an indication depends on the extent of any prior understanding about the interpretation to be given to information being exchanged as between the sender and the recipient of the indication. For example, if it is understood prior to a communication between a sender and a recipient that an indication of an information element will take the form of a database key for an entry in a particular table of a predetermined database containing the information element, then the sending of the database key is all that is required to effectively convey the information element to the recipient, even though the information element itself was not transmitted as between the sender and the recipient of the indication.

In the context of the present specification, the expression "communication network" is intended to include a telecommunications network such as a computer network, the Internet, a telephone network, a Telex network, a TCP/IP data network (e.g., a WAN network, a LAN network, etc.), and the like. The term "communication network" includes a wired network or direct-wired connection, and wireless media such as acoustic, radio frequency (RF), infrared and other wireless media, as well as combinations of any of the above.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "server" and "third server" is not intended to imply any particular order, type, chronology, hierarchy or ranking (for example) of/between the servers, nor is their use (by itself) intended to imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
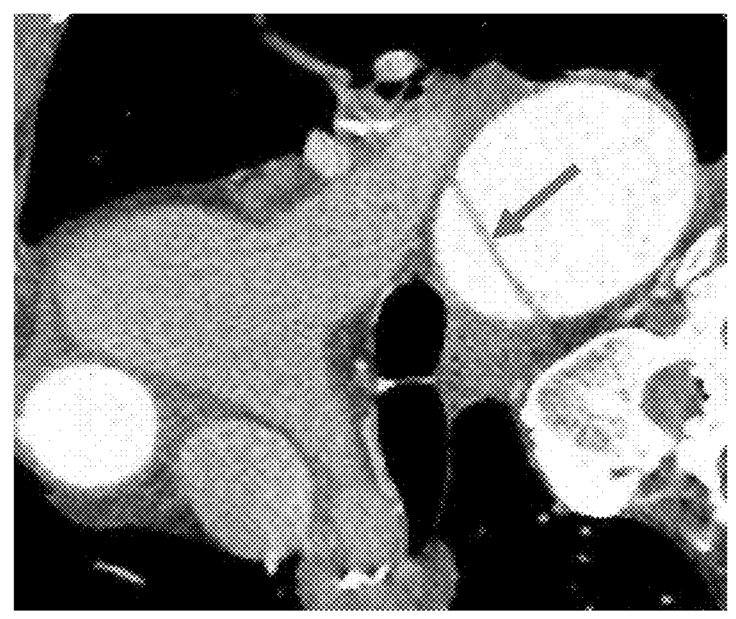
FIG. 1 depicts a slice of an aorta obtained from static computational tomography (CT) imaging showing presence of a dissection in the descending portion of the aorta.

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudo-code, and the like represent various processes which may be substantially represented in computer-readable media and so executed by a computer or processor, whether or not such computer or processor is explicitly shown.

The functions of the various elements shown in the figures, including any functional block labeled as a "processor" or a "graphics processing unit", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. In some non-limiting embodiments of the present technology, the processor may be a general-purpose processor, such as a central processing unit (CPU) or a processor dedicated to a specific purpose, such as a graphics processing unit (GPU). Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Figure 2:
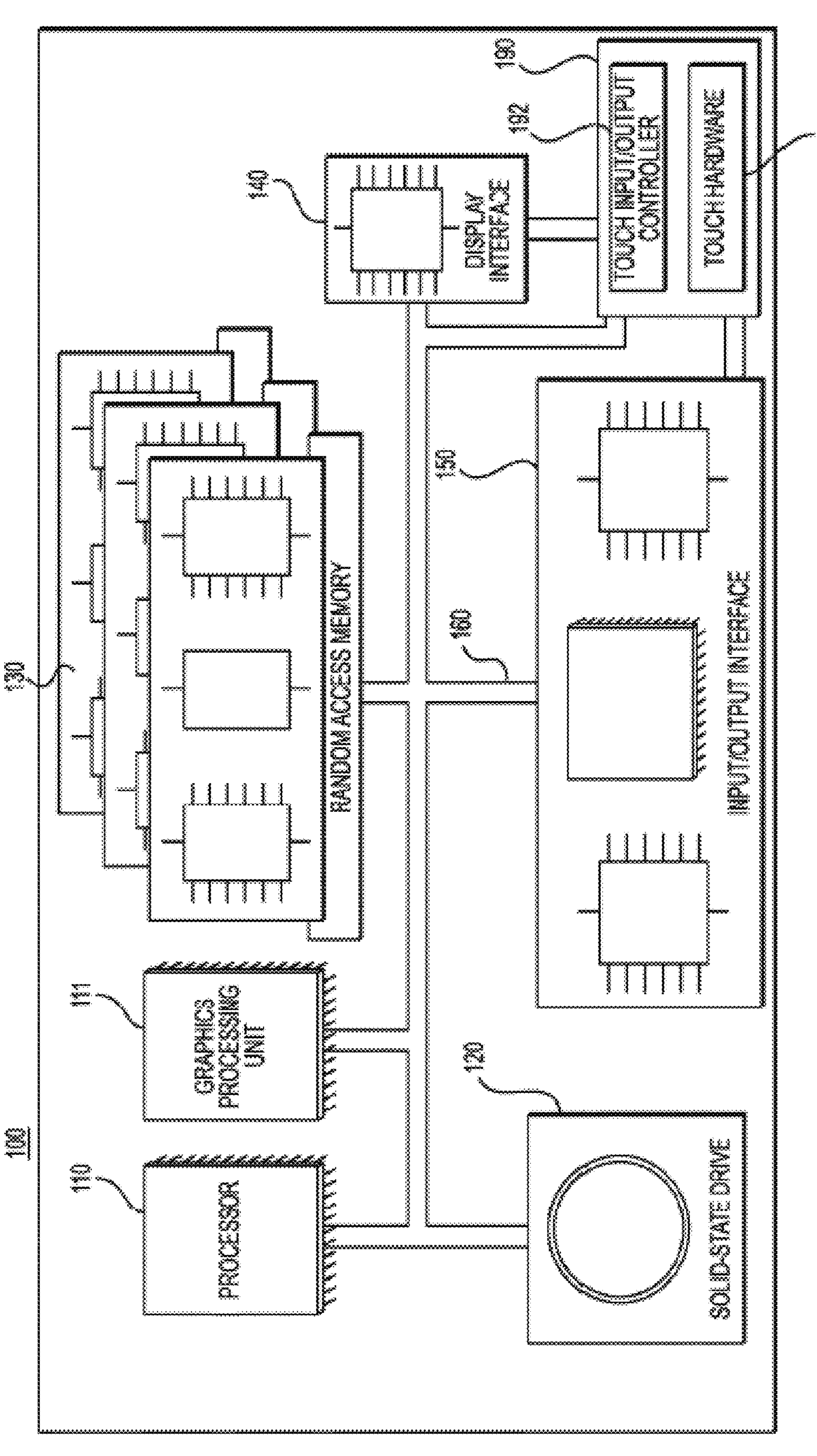
FIG. 2 depicts a schematic diagram of an electronic device in accordance with one or more non-limiting embodiments of the present technology.

With reference to FIG. 2, there is illustrated a schematic diagram of an electronic device 100 suitable for use with some non-limiting embodiments of the present technology.

Electronic Device

The electronic device 100 comprises various hardware components including one or more single or multi-core processors collectively represented by processor 110, a graphics processing unit (GPU) 111, a solid-state drive 120, a random-access memory 130, a display interface 140, and an input/output interface 150.

Communication between the various components of the electronic device 100 may be enabled by one or more internal and/or external buses 160 (e.g., a PCI bus, universal serial bus, IEEE 1394 "Firewire" bus, SCSI bus, Serial-ATA bus, etc.), to which the various hardware components are electronically coupled.

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 2, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the electronic device 100 in addition or in replacement of the touchscreen 190.

According to implementations of the present technology, the solid-state drive 120 stores program instructions suitable for being loaded into the random-access memory 130 and executed by the processor 110 and/or the GPU 111 for performing in vivo strain mapping of an aortic dissection. For example, the program instructions may be part of a library or an application.

The electronic device 100 may be implemented in the form of a server, a desktop computer, a laptop computer, a tablet, a smartphone, a personal digital assistant or any device that may be configured to implement the present technology, as it may be understood by a person skilled in the art.

System

Figure 3:
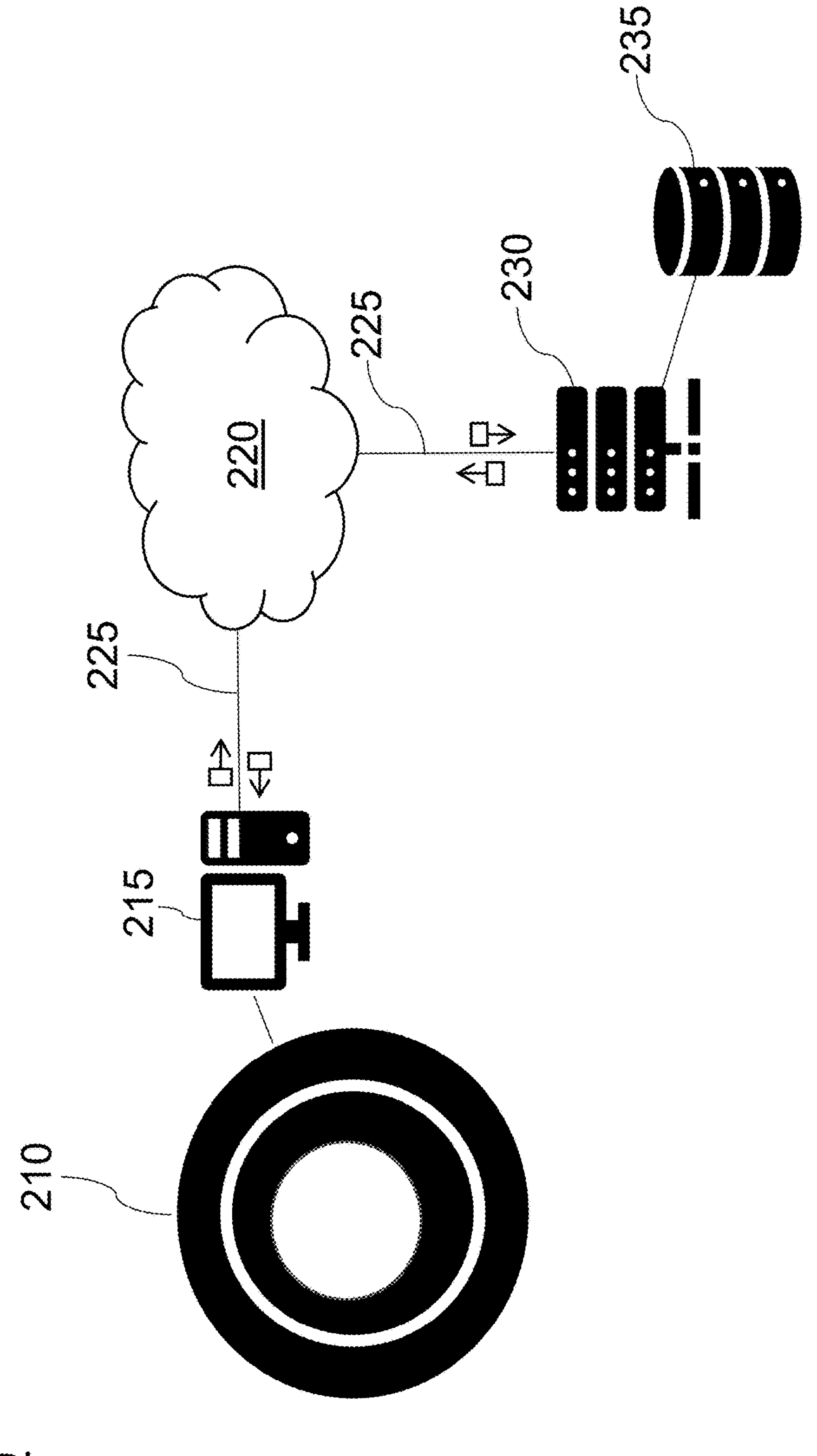
FIG. 3 depicts a schematic diagram of a communication system in accordance with one or more non-limiting embodiments of the present technology.

Referring to FIG. 3, there is shown a schematic diagram of a communication system 200, which will be referred to as the system 200, the system 200 being suitable for implementing non-limiting embodiments of the present technology. It is to be expressly understood that the system 200 as illustrated is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 200 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition it is to be understood that the system 200 may provide in certain instances simple implementations of the present technology, and that where such is the case they have been presented in this manner as an aid to understanding. As persons skilled in the art would understand, various implementations of the present technology may be of a greater complexity.

The system 200 comprises inter alia a medical imaging apparatus 210 associated with a workstation computer 215, and a server 230 coupled over a communications network 220 via respective communication links 225 (not separately numbered).

Medical Device

The medical imaging apparatus 210 is configured to inter alia acquire, at different time points, a plurality of images of a blood vessel of a given subject such that a representation of the blood vessel of the given subject may be subsequently generated.

In one or more embodiments, the medical imaging apparatus 210 comprises an ECG-gated medical imaging apparatus.

The medical imaging apparatus 210 may comprise one of: a computed tomography (CT) scanner, a magnetic resonance imaging (MRI) scanner, a 3D ultrasound or the like.

In some embodiments of the present technology, the medical imaging apparatus 210 may comprise a plurality of medical imaging apparatuses, such as one or more of a computational tomography (CT) scanner, a magnetic resonance imaging (MRI) scanner, a 3D ultrasound, and the like.

The medical imaging apparatus 210 may be configured with specific acquisition parameters for acquiring the plurality of images of a blood vessel during over a cardiac cycle.

As a non-limiting example, in one or more embodiments where the medical imaging apparatus 210 is implemented as a CT scanner, a CT protocol comprising pre-operative retrospectively gated multidetector CT (MDCT—64-row multi-slice CT scanner) with variable dose radiation to capture the R-R interval may be used.

As another non-limiting example, in one or more embodiments where the medical imaging procedure comprises a MRI scanner, the MR protocol can comprise steady state T2 weighted fast field echo (TE=2.6 ms, TR=5.2 ms, flip angle 110 degree, fat suppression (SPTR), echo time 50 ms, maximum 25 heart phases, matrix 256×256, acquisition voxel MPS (measurement, phase and slice encoding directions) 1.56/1.56/3.00 mm and reconstruction voxel MPS 0.78/0.78/1.5), or similar cine acquisition of the portion of aorta under study, axial slices. The medical imaging apparatus 210 includes or is connected to a workstation computer 215 for inter alia data transmission.

Workstation Computer

The workstation computer 215 is configured to inter alia: (i) control parameters of the medical imaging apparatus 210 and cause acquisition of images; and (ii) receive and process the plurality of images from the medical imaging apparatus 210.

In one or more embodiments. the workstation computer 215 may receive images in raw format and perform a tomographic reconstruction using known algorithms and software.

The implementation of the workstation computer 215 is known in the art. The workstation computer 215 may be implemented as the electronic device 100 or comprise components thereof, such as the processor 110, the graphics processing unit (GPU) 111, the solid-state drive 120, the random-access memory 130, the display interface 140, and the input/output interface 150.

In one or more other embodiments, the workstation computer 215 may be integrated at least in part into the medical imaging apparatus 210.

In one or more embodiments, the workstation computer 215 is configured according to the Digital Imaging and Communications in Medicine (DICOM) standard for communication and management of medical imaging information and related data.

In one or more embodiments, the workstation computer 215 may store the images in a local database (not illustrated).

The workstation computer 215 is connected to a server 230 over the communications network 220 via a respective communication link 225. In one or more embodiments, the workstation computer 215 may transmit the images and/or multiphase stack to the server 230 and the database 235 for storage and processing thereof.

In one embodiment, the multiphase stack comprises a plurality of 3D images each taken at a respective and different point in time or phase. At each phase, the 3D image comprises a plurality of voxels each having associated thereto a respective 3D position and a parameter value such as a color value, a grayscale value, an intensity value, or the like.

Server

The server 230 is configured to inter alia: (i) receive a plurality of images of a dissected blood vessel having been acquired by the medical imaging apparatus 210; (ii) generate, using the plurality of images of the dissected blood vessel, a multiphase stack, each phase corresponding to a given moment in the cardiac cycle; (iii) generate, using the plurality of images and the multiphase stack, a 3D geometrical model of the dissected blood vessel; (iv) generate, using the 3D geometrical model of the dissected vessel, a surface mesh of the dissected blood vessel comprising a vessel wall surface mesh and a dissection flap surface mesh; (v) determine, using the surface mesh of the dissected blood vessel and the multiphase stack, a nodal displacement of the surface mesh throughout the cardiac cycle to obtain a local deformation of the dissected blood vessel at each phase; (vi) determine a strain map of the dissected blood vessel at each phase of the cardiac cycle; and (vii) generate an interactive model of the dissected blood vessel using the strain map and the 3D geometrical model of the dissected blood vessel.

How the server 230 is configured to do so will be explained in more detail herein below.

The server 230 can be implemented as a conventional computer server and may comprise some or all of the components of the electronic device 100 illustrated in FIG. 2. In an example of one or more embodiments of the present technology, the server 230 can be implemented as a Dell™ PowerEdge™ Server running the Microsoft™ Windows Server™ operating system. Needless to say, the server 230 can be implemented in any other suitable hardware and/or software and/or firmware or a combination thereof. In the illustrated non-limiting embodiment of present technology, the server 230 is a single server. In alternative non-limiting embodiments of the present technology, the functionality of the server 230 may be distributed and may be implemented via multiple servers (not illustrated).

The implementation of the server 230 is well known to the person skilled in the art of the present technology. However, briefly speaking, the server 230 comprises a communication interface (not illustrated) structured and configured to communicate with various entities (such as the workstation computer 215, for example and other devices potentially coupled to the network 220) via the communications network 220. The server 230 further comprises at least one computer processor (e.g., a processor 110 or GPU 111 of the electronic device 100) operationally connected with the communication interface and structured and configured to execute various processes to be described herein.

In one or more embodiments, the server 230 may be implemented as the electronic device 100 or comprise components thereof, such as the processor 110, the graphics processing unit (GPU) 111, the solid-state drive 120, the random-access memory 130, the display interface 140, and the input/output interface 150.

Database

The database 235 is directly connected to the server 230 but, in one or more alternative implementations, the database 235 may be communicatively coupled to the server 230 via the communications network 220 without departing from the teachings of the present technology. Although the database 235 is illustrated schematically herein as a single entity, it will be appreciated that the database 235 may be configured in a distributed manner, for example, the database 235 may have different components, each component being configured for a particular kind of retrieval therefrom or storage therein.

The database 235 may be a structured collection of data, irrespective of its particular structure or the computer hardware on which data is stored, implemented or otherwise rendered available for use. The database 235 may reside on the same hardware as a process that stores or makes use of the information stored in the database 230 such as the server 230, or it may reside on separate hardware, such as on one or more other electronic devices (not shown) directly connected to the server 230 and/or connected to the communications network 220. The database 230 may receive data from the server 230 for storage thereof and may provide stored data to the server 230 for use thereof.

The database 235 is configured to inter alia: (i) store images having been acquired by the medical imaging apparatus 210; (ii) store DICOM multiphase stacks; (iii) store 3D geometrical models of blood vessels; (iv) store strain maps of dissected blood vessels; and (v) store interactive models of dissected blood vessels.

Communication Network

In some embodiments of the present technology, the communications network 220 is the Internet. In alternative non-limiting embodiments, the communication network 220 can be implemented as any suitable local area network (LAN), wide area network (WAN), a private communication network or the like. It should be expressly understood that implementations for the communication network 220 are for illustration purposes only. How a communication link 225 (not separately numbered) between the workstation computer 215 and/or the server 230 and/or another electronic device (not illustrated) and the communications network 220 is implemented will depend inter alia on how each of the medical imaging apparatus 210, the workstation computer 215, and the server 230 is implemented.

The communication network 220 may be used in order to transmit data packets amongst the workstation computer 215, the server 230 and the database 235. For example, the communication network 220 may be used to transmit requests between the workstation computer 215 and the server 230.

In one embodiment, the server 230 may be part of a Picture Archiving and Communication System (PACS).

In another embodiment, the server 230 may be omitted. In this case, the workstation computer 215 is in communication with or connected to the database 235, and is configured to inter glia: (i) receive a plurality of images of a dissected blood vessel having been acquired by the medical imaging apparatus 210; (ii) generate, using the plurality of images of the dissected blood vessel, a multiphase stack, each phase corresponding to a given moment in the cardiac cycle; (iii) generate, using the plurality of images and the multiphase stack, a 3D geometrical model of the dissected blood vessel; (iv) generate, using the 3D geometrical model of the dissected vessel, a surface mesh of the dissected blood vessel comprising a vessel wall surface mesh and a dissection flap surface mesh; (v) determine, using the surface mesh of the dissected blood vessel and the multiphase stack, a nodal displacement of the surface mesh throughout the cardiac cycle to obtain a local deformation of the dissected blood vessel at each phase; (vi) determine a strain map of the dissected blood vessel at each phase of the cardiac cycle; and (vii) generate an interactive model of the dissected blood vessel using the strain map and the 3D geometrical model of the dissected blood vessel.

Aortic Dissection Strain Mapping Procedure

Figure 4:
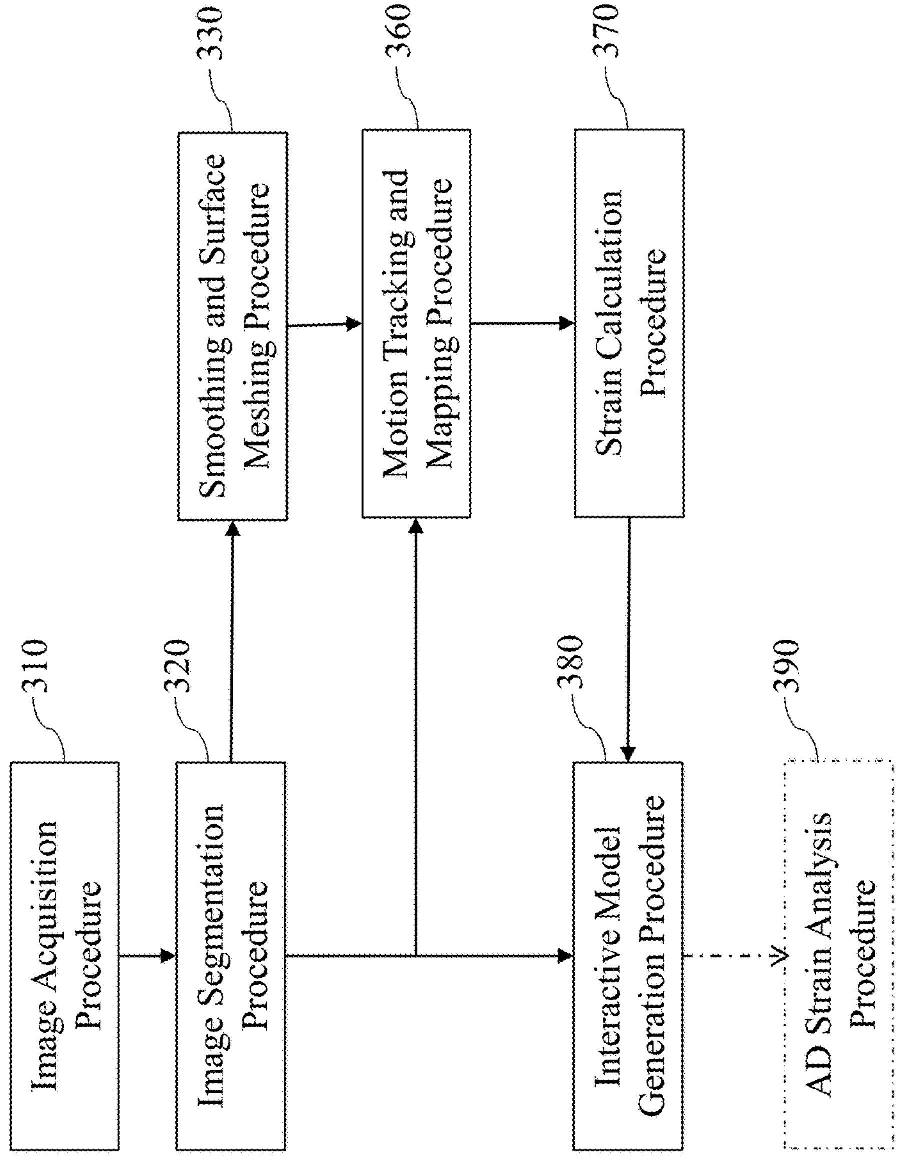
FIG. 4 depicts a schematic diagram of an aortic dissection (AD) strain mapping procedure, the AD strain mapping procedure being executed within the system of FIG. 3 in accordance with one or more non-limiting embodiments of the present technology.

Now turning to FIG. 4, there is a illustrated a schematic diagram of an aortic dissection (AD) strain mapping procedure 300 in accordance with one or more non-limiting embodiments of the present technology.

The AD strain mapping procedure 300 is executed within the system 200 of FIG. 3. In one or more embodiments, the AD strain mapping procedure 300 may be executed by the server 230. In one or more other embodiments, the AD strain mapping procedure 300 may be executed by the workstation computer 215 connected to the medical imaging apparatus 210. It is contemplated that some procedures of the AD strain mapping procedure 300 may be executed in parallel by the server 230 or by electronic devices (such as the workstation computer 215) as will be recognized by persons skilled in the art.

The purpose of the AD strain mapping procedure 300 is to receive images of a dissected blood vessel having been acquired during a cardiac cycle of a given patient, and generate, using the received images of the dissected blood vessel, a strain map of the dissected blood vessel of the given patient.

The AD strain mapping procedure 300 enables visualizing and assessing the mutual interaction between the flow channels (e.g., true and false lumen) created by the dissection flap, such as presence of blood in the false lumen that pressurizes the false lumen and causes compression of the true lumen over a cardiac cycle, which may lead to complications due to the blood supply to downstream organs being limited.

The AD strain mapping procedure 300 comprises inter alia an image acquisition procedure 310, an image segmentation procedure 320, a smoothing and surface meshing procedure 330, a motion tracking and mapping procedure 360, a strain calculation procedure 370, and an interactive model generation procedure 380.

Image Acquisition

The image acquisition procedure 310 is configured to inter alia: (i) receive images of a dissected blood vessel of a patient having been acquired during a cardiac cycle; and (ii) generate, using the received images of the dissected blood vessel, a multiphase stack thereof.

In one or more embodiments, the images of the dissected blood vessel are acquired from a subject known to have an aortic dissection, which may have been diagnosed by a physician. In one or more other embodiments, the images of the dissected blood vessel may have been acquired without previous knowledge of an aortic dissection and may be, for example, detected during the image segmentation procedure 320.

During the image acquisition procedure 310, a plurality of images of a blood vessel, such as an aorta of a given subject, are received. The plurality of images may be received from the workstation computer 215, directly from the medical imaging apparatus 210, from a database such as database 235, etc. In one or more embodiments, the plurality of images of the blood vessel comprise images of an aorta having a dissection flap. It will be appreciated that the type of aortic dissection in the dissected blood vessel is not limited.

In one or more embodiments where the medical imaging apparatus 210 comprises a CT scanner, the CT protocol for CT image acquisition can comprise pre-operative retrospectively gated MDCT (64-row multi-slice CT scanner) with variable dose radiation to capture the R-R interval. In one embodiment where the medical imaging apparatus 210 is a MRI scanner, the MR protocol can comprise steady state T2 weighted fast field echo (TE=2.6 ms, TR=5.2 ms, flip angle 110 degree, fat suppression (SPIR), echo time 50 ms, maximum 25 heart phases 2, matrix 256×256, acquisition voxel MPS 1.56/1.56/3.00 mm and reconstruction voxel MPS 0.78/0.78/1.5), or similar cine acquisition of the portion of aorta under study, axial slices.

The image acquisition procedure 310 organizes the plurality of images in a multiphase stack. In one embodiment, the plurality of images is organized in phases according to a Digital Imaging and Communications in Medicine (DICOM) stack, the implementation of which is known in the art.

In one or more embodiments, each phase of the multiphase stack corresponds to a time instance in the cardiac cycle of the given patient.

The image acquisition procedure 310 outputs the multiphase stack.

Image Segmentation

The image segmentation procedure 320 is configured to inter alia: (i) receive as an input images corresponding to one phase of the multiphase stack; (ii) generate, based on the received input images, a 3D geometrical model of the dissected blood vessel.

In one or more embodiments, the input images corresponding to one phase of the multiphase stack comprise an indication of the dissection flap. As a non-limiting example, the indication may be provided by an operator via the input/output interface 150 such as a keyboard. The indication of the dissection flap may be received at the same time as the multiphase stack or at a different time.

In one or more alternative embodiments, the image segmentation procedure 320 comprises the automatic identification of a dissection flap. In this case, the image segmentation procedure 320 may use one or more machine learning (ML) models having been trained to recognize dissection flaps in images of blood vessels. The image segmentation procedure 320 may use ML models to perform segmentation by classifying pixels as belonging to healthy tissues, dissected portions, true lumen, false lumen and/or the like.

The image segmentation procedure 320 thus comprises the reception of one phase of the multiphase stack with an indication of the true lumen and the false lumen in the dissected blood vessel.

The image segmentation procedure 320 uses segmentation techniques, which are known to the person skilled in the art, to identify pixels or voxels belonging to an object such as the blood vessel and/or locating those that form the boundary of the blood vessel to generate a 3D geometrical model of at least a portion of the blood vessel. It should be understood that any adequate segmentation technique can be used. The image segmentation procedure 320 may segment the stack based on one or more of: pixel intensity, texture, and/or other attributes, using deformable models and techniques such as, but not limited to, low-level segmentation (thresholding, region growing, etc.), model based segmentation (multispectral, feature maps, dynamic programming, counter following), statistical techniques, fuzzy techniques as well as other techniques known in the art. In one or more other embodiments, at least a portion of the image segmentation procedure 320 may be performed by a human operator by manually drawing the boundaries of the dissected blood vessel.

The image segmentation procedures 320 generates, using the multiphase stack: a 3D geometrical model of the dissected blood vessel, the 3D geometrical model of the blood vessel comprising a representation of at least the wall(s) of the blood vessel and the wall of the dissection flap.

In one or more embodiments, the 3D geometrical model of the dissected vessel comprises at least: a true lumen, a false lumen, the dissection flap, and, when present in the images, the healthy (non-dissected) portion of the vessel.

The 3D geometrical model of the dissected blood vessel and the 3D geometrical model of the blood vessel comprising a representation of the blood vessel and of the dissection flap may correspond to or may be used to obtain a 3D geometrical representation of the true lumen and the false lumen.

In one or more embodiments, the image segmentation procedure 320 generates, based on a first or given phase of the multiphase stack, corresponding to a given time in the cardiac cycle identified as phase 0, the 3D geometrical model of the dissected blood vessel. It will be appreciated that any phase of the multiphase stack may be used to generate the 3D geometrical model of the dissected blood vessel.

The false lumen in the dissected blood vessel corresponds to the lumen created by the dissection flap which is separated from the true lumen in the blood vessel.

Figure 5:
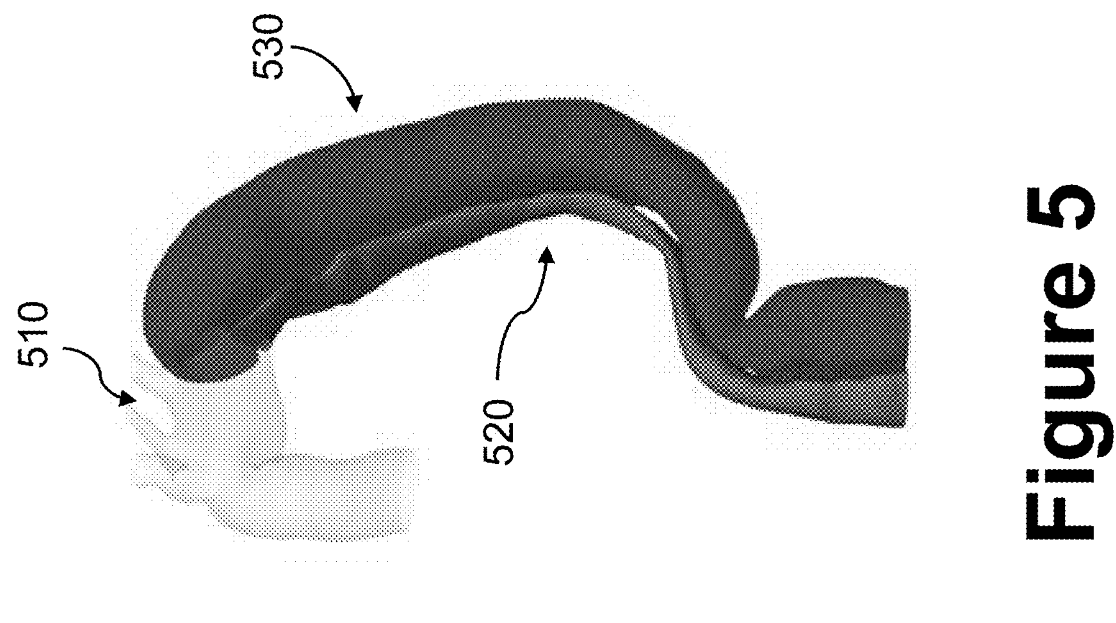
FIG. 5 illustrates an example of a 3D geometrical model of a residual type B AD in the descending aorta, after surgery for type A AD, the example being illustrated in accordance with one or more non-limiting embodiments of the present technology.

FIG. 5 depicts an example of a 3D geometrical model 500 of a residual type B AD after surgery for type A AD (surgical repair of the ascending aorta) as output by the image segmentation procedures 320. The 3D geometrical model 500 comprises a presentation of: a repaired ascending aorta and aortic arch 510, the true lumen 520 and the false lumen 530. In the imaged portion of this AD, an entry tear is identified past left subclavian artery.

Turning back to FIG. 4, the image segmentation procedure 320 outputs the 3D geometrical model of the dissected blood vessel.

Smoothing and Surface Meshing

The smoothing and surface meshing procedure 330 is configured to inter alia: (i) receive the 3D geometrical model of the dissected blood vessel comprising the wall of blood vessel and the dissection flap; (ii) generate, using the 3D geometrical model of the dissected vessel, a surface mesh of the dissected blood vessel, the surface mesh of the dissected blood vessel comprising a blood vessel wall surface mesh and a dissection flap surface mesh. In one embodiment, the surface mesh of the dissected blood vessel corresponds to a discrete representation of the 3D geometrical model of the dissected vessel which comprises nodes, vertices, edges, faces and/or the like.

In one or more embodiments, the surface mesh of the dissected blood vessel comprises a surface mesh of the true lumen and a surface mesh of the false lumen of the dissected blood vessel.

The smoothing and surface meshing procedure 330 receives as input the 3D geometrical model of the dissected blood vessel which comprises a representation of the wall of the blood vessel and of the dissection flap.

In one embodiment, the smoothing and surface meshing procedure 330 filters or denoises the 3D geometrical model of the dissected blood vessel before generating the surface mesh of the dissected blood vessel.

In the same or another embodiment, the smoothing and surface meshing procedure 330 smooths the 3D geometrical model of the dissected blood vessel before generating the surface mesh of the dissected blood vessel.

It should be understood that any adequate method for generating the surface mesh of the dissected blood vessel from the 3D geometrical model of the dissected blood vessel may be used. For example, polygon modeling may be used.

In one embodiment, the surface mesh of the 3D geometrical model of the dissected blood vessel is in the form of discretized geometry of small polygon elements, such as small triangular elements, or shells. It will be appreciated that in alternative embodiments of the present technology, the smoothing of the 3D geometrical model may be optional.

In one embodiment, the smoothing and surface meshing procedure 330 uses a Taubin filter for smoothing and/or a quadric edge collapse decimation to reduce a number of shells. As a non-limiting example, the surface mesh of the dissected blood vessel may have approximately 4,000 triangular shell elements.

In one embodiment, the resolution of the surface mesh of the 3D geometrical model of the dissected blood vessel is at least as big as the pixel size. In one embodiment, the surface mesh of the dissected blood vessel is a deformable mesh.

The smoothing and surface meshing procedure 330 obtains the surface mesh of the blood vessel wall and the surface mesh of the dissection flap which corresponds to the surface mesh of a wall of the true lumen and the surface mesh of a wall of the false lumen of the dissected blood vessel.

In one embodiment, a surface mesh of the true lumen and a surface mesh of the false lumen are generated in order to obtain the surface mesh of the dissection flap.

The smoothing and surface meshing procedure 330 outputs the surface mesh of the dissected blood vessel, the surface mesh of the dissected blood vessel comprising a vessel wall surface mesh and a dissection flap surface mesh.

Motion Tracking and Mapping

The motion tracking and mapping procedure 360 is configured to inter alia: (i) receive the surface mesh of the dissected blood vessel, the surface mesh of the dissected blood vessel comprising the surface mesh of the wall of blood vessel and the surface mesh of the dissection flap; (ii) receive the multiphase stack of the dissected blood vessel for all phases; (iii) track and map each voxel position of the surface mesh nodes for the first phase (which was used for generating the surface mesh of the dissected blood vessel) to all the subsequent phases of the cardiac cycle to obtain a nodal displacement of the surface mesh throughout the cardiac cycle; and (iv) determine, using the displaced nodes of the surface mesh, a local deformation of the surface mesh of the dissected blood vessel at all phases of the cardiac cycle.

The motion tracking and mapping procedure 360 receives as inputs the surface mesh of the 3D geometrical model of the dissected blood vessel outputted by the image segmentation procedure 320 and the multiphase stack of images for all phases outputted by the image acquisition procedure 310. In one or more embodiments, the motion tracking and mapping procedure 360 receives the 3D geometrical model and the multiphase stack from the database 235.

In one embodiment, the motion tracking and mapping procedure 360 is executed by using the software Virtual Touch Aortic Aneurysm (ViTAA™) of which embodiments are described in International Patent Application Publication WO 2018/068153 A1.

The motion tracking and mapping procedure 360 uploads the surface mesh of the 3D geometrical model of the dissected blood vessel created for the first phase onto the multiphase stack.

The motion tracking and mapping procedure 360 first imports the surface mesh of the dissected blood vessel for the first phase into the 3D space of the image of the first phase, thereby identifying, for each node of the surface mesh of the dissected blood vessel for the first phase, a respective voxel of the image of the first phase. For each node of the surface mesh of the dissected blood vessel for the first phase, the voxel position of its corresponding voxel of the first phase is assigned to the node. Then the motion tracking and mapping procedure 360 tracks, for each node of the surface mesh of the dissected blood vessel, the position of its corresponding voxel throughout the subsequent phases and thereby maps each voxel position of the surface mesh of the dissected blood vessel for the first phase to all the subsequent phases. The position of all the voxels at the different phases is mapped back to the surface mesh for the first phase, where each node position of the geometry at the first phase is associated with node positions corresponding to all the subsequent phases, thereby obtaining a respective deformed surface mesh for each phase. Thus, nodal displacement throughout the cardiac cycle, i.e., different phases, may be determined for the true lumen and the false lumen and, consequently, the dissection flap. As a result, a deformed surface mesh is obtained for each phase and each node of a deformed surface mesh for a given phase is assigned the voxel position of its corresponding voxel in the image of the given phase.

In one or more embodiments, the mapping of the voxel positions of the surface mesh of the dissected blood vessel for the first phase to all the subsequent phases is performed using an optical flow (OF) algorithm. It will be appreciated that other techniques known in the art may be used to track nodal displacement.

In one embodiment, the motion tracking and mapping procedure 360 follows the displacement of an object, such as a given point, between images taken at subsequent time steps by detecting the grayscale feature corresponding to the object and computing its velocity. In one or more embodiments, the motion tracking and mapping procedure 360 uses machine learning models having been trained for tracking objects in images.

As a non-limiting example, for CT images, the nodes corresponding to the first phase will have corresponding node positions for all the subsequent phases.

From the map of the displaced nodes, the motion tracking and mapping procedure 360 generates a respective mesh for each phase. The position of all the voxels at the different phases is mapped back to the surface mesh for the first phase so that each node position of the surface mesh geometry at the first phase is associated with node positions corresponding to all the subsequent phases, i.e., the initial surface mesh, i.e. the surface mesh for the first phase, is used to track the corresponding voxels at subsequent phases and generate deformed surface meshes at all phases by updating the coordinate location (or displacement) for each node of the initial surface mesh.

The motion tracking and mapping procedure 360 outputs the local deformation at each phase of the surface mesh for the true lumen and the false lumen in the dissected blood vessel. In one embodiment, the local deformation for a given phase comprises the voxel position of each node of the surface mesh for the given phase, i.e., for each node of the surface mesh, the position in the given phase of the voxel that corresponds to the node. In another embodiment, the local deformation for a given phase comprises the change of voxel position for each node of the surface mesh between a previous phase to the given phase, such as the change of voxel position from the first phase to the given phase.

Strain Calculation

The strain calculation procedure 370 is configured to inter alia: (i) receive the local deformation of the surface mesh of the dissected blood vessel comprising local deformations of the blood vessel wall and of the dissection flap at each phase of the cardiac cycle; (ii) the surface mesh of the vessel wall and dissection flap at the first phase of the cardiac cycle; and (iii) determine, based on the local deformation and the surface mesh, a strain distribution at each phase of the cardiac cycle.

The strain calculation procedure 370 receives the local deformation of the blood vessel wall and the local deformation of the dissection flap at each phase of the cardiac cycle, corresponding to local deformations of the true lumen and the false lumen in the dissected blood vessel.

In one or more embodiments, the strain calculation procedure 370 receives the local deformation of the blood vessel wall and the local deformation of dissection flap at each phase of the cardiac cycle from the motion tracking and mapping procedure 360. In one or more other embodiments, the strain calculation procedure 370 receives the local deformation of the blood vessel wall and the local deformation of dissection flap at each phase of the cardiac cycle from the database 235.

The strain calculation procedure 370 uses continuum mechanics techniques to compute in vivo strains based on the local kinematics at each phase of the surface mesh of the vessel wall and the dissection flap. The strain calculation procedure 370 calculates the strain at each node of the surface mesh for each phase of the cardiac cycle, resulting in a strain distribution, or strain map, at each phase of the cardiac cycle.

As a non-limiting example, with reference to one triangular element of the surface mesh at the first phase of the cardiac cycle, a reference coordinate system is defined with center at node 1 and three vectors defined as $A_1$ from node 1 to node 2, $A_2$ from node 1 to node 3 and $A_3$, a unit vector perpendicular to the first two. These nodes and vectors define the undeformed reference configuration of the triangular element. $A_1$, $A_2$ and $A_3$ are then mapped into the corresponding spatial vectors $a_1$, $a_2$, $a_3$ centered at the new position of node 1 in the current deformed configuration for each subsequent phase of the cardiac cycle. With the in-plane vectors ($A_1$, $A_2$ and $a_1$, $a_2$) known from the mesh tracking through each subsequent phase and an additional tissue incompressibility constraint imposed on the out of plane vector $a_3$, all the components of the deformation gradient tensor F are computed based on the system of equations $[a_k]^i = F^i_I$, with k=1, 2, 3, $[A_k]^I$ the I-th component of $A_k$, $[a_k]^i$ the i-th component of $a_k$ and $F^i_I$ the iI-th component of the tensor F. The person skilled in the art will appreciate that while the present example refers to a triangular shell element, shell elements having a shape other than a triangular shape may be used.

In one embodiment, the strain calculation procedure 370 takes the deformation gradient F and computes the right Cauchy-Green deformation tensor $C = F^T \cdot F$ and the non-linear Green-Lagrange strain tensor as $E = \frac{1}{2}(C - I)$, which is then diagonalized to obtain principal strain values.

The strain calculation procedure 370 computes the principal strain values along the principal strain directions as eigenvalues of the diagonalized Green-Lagrange strain tensor. In one or more embodiments, the strain calculation procedure 370 determines the principal strain values along the principal strain directions for the surface mesh of the blood vessel wall and dissection flap to obtain a distribution of strain measurements or strain map at each phase of the cardiac cycle as representative of relative displacement of regions of the outer wall of the blood vessel and of the dissection flap. The strain calculation procedure 370 outputs a set of strain maps for the cardiac cycle, where each strain map includes the principal strain values corresponding to a respective phase of the cardiac cycle.

In one or more embodiments, the strain calculation procedure 370 determines the projection of the strain in the principal directions of curvature to obtain a circumferential strain value and an axial strain value for each displaced nodes tracked on the surface mesh of the dissected blood vessel.

In one or more embodiments, the strain calculation procedure 370 determines a maximum strain map by using the set of strain maps. The strain calculation procedure 370 determines the maximal principal strain values as the maximum of the three principal strain values along the principal strain directions at each phase of the cardiac cycle to obtain a distribution of the maximal principal strain measurements or maximum principal strain map over the cardiac cycle for the surface mesh of the blood vessel wall and the dissection flap.

Thus, the strain calculation procedure 370 outputs at least one of: a set of strain maps including the principal strain values over the cardiac cycle and a maximum principal strain map including the maximum principal strain values over the cardiac cycle.

It will be appreciated that the number of strain maps in the set of strain maps is not limited and depends on the number of phases queried over the cardiac cycle during the image acquisition procedure 310.

It should be understood that the number of values of principal strain or maximum principal strain is not limited and depends on the number of displaced nodes defining the tracking surface mesh.

As a non-limiting example, in one embodiment where the ECG-gated dynamic acquisition procedure generates a multiphase DICOM stack that comprises 10 phases, the strain calculation procedure 370 outputs 10 strain maps, one at each phase of the cardiac cycle, as well as a final map for the maximum principal strain over the cardiac cycle.

As another non-limiting example, in one or more embodiments where the image acquisition procedure 310 comprises a dynamic MRI acquisition with low resolution, the final strain map may be used in combination with one or more of a T1-weighted spin-echo (black-blood) MRI acquisition, a 4D-flow MRI acquisition, and a phase-contrast MRI acquisition in order to better identify the presence and location of small entry and/or re-entry tears along the intimal dissection flap.

Interactive Model Generation

The interactive model generation procedure 380 is configured to inter alia: (i) receive at least one of the set of strain maps and the maximum strain map of the dissected blood vessel over the cardiac cycle; (ii) receive the 3D geometrical model of the dissected blood vessel; and (iii) generate, using the 3D geometrical model of the dissected blood vessel and at least one of the set of strain maps and the maximum strain map, an interactive model of the dissected blood vessel.

The interactive model generation procedure 380 generates, using the 3D geometrical model and the strain map at different times in the cardiac cycle, an interactive model of the dissected blood vessel comprising strain values for each phase of the cardiac cycle.

Additionally or alternatively, the interactive model generation procedure 380 generates, using the 3D geometrical model and the maximum strain map, an interactive model of the dissected blood vessel comprising maximum strain values for the whole cardiac cycle. It will be appreciated that the maximum strain map is determined based on the set of strain maps.

In one or more embodiments, the interactive model generation procedure 380 superimposes the final strain map to the original image acquisition or any of the mentioned additional acquisitions when available, therefore resulting in image fusion and combined information displayed simultaneously.

In one or more embodiments, the interactive model comprises the 3D model of the dissected blood vessel where strains at different locations on the dissected blood vessel may be visualized at different times during the cardiac cycle. The interactive model generation procedure 380 may color code different values of strain and enable displaying strain using different types of visual indicators.

The interactive model enables displaying a strain map of the aortic wall and dissection flap at each phase of the cardiac cycle to allow comparison of dissected and non-dissected regions (when present on images) of the aorta in order to support the assessment of individual aortic dissections and the differentiation between the true lumen and the false lumen.

Further, the interactive model may be used to visualize the dissected blood vessel comprising the true lumen, false lumen and strain map at different angles, location and level of detail, display images having been used to generate the 3D representation of the dissected blood vessel, display information related to the dissected blood vessel and the given patient, as well as any other relevant information that may be used by a medical professional to assess the dissected blood vessel.

In one or more embodiments, the AD strain mapping procedure 300 is repeated for the given patient at subsequent times (i.e., after acquisition of new images of the dissected blood vessel of the given patient) and the results (i.e., strain maps and geometrical models) may be included in the interactive model such that the temporal evolution of the strains and geometry of the dissected blood vessel may be assessed and compared.

The interactive model generation procedure 380 outputs the interactive model of the dissected blood vessel comprising the strain maps over the cardiac cycle.

In one or more embodiments, the interactive model generation procedure 380 transmits the interactive model for display on a display interface, such as on a display interface 140 of the workstation computer 215 or the electronic device 100.

In one or more embodiments, the AD strain mapping procedure 300 comprises the AD strain analysis procedure 390.

AD Strain Analysis

The AD strain analysis procedure 390 is configured to perform further analysis using the strain map of the dissected blood vessel outputted by the strain calculation procedure 370 and the interactive model generation procedure 380.

In one or more embodiments, the AD strain analysis procedure 390 may use one or more machine learning (ML) models having been trained to perform analysis of aortic dissections. As a non-limiting example, such the one or more ML models may be trained on the output of the AD strain mapping procedure 300 in combination with clinical and medical data.

In one or more embodiments, the AD strain analysis procedure 390 performs analysis of the strain map of the aortic wall and dissection flap at each phase of the cardiac cycle to allow comparison of dissected and non-dissected regions (when present on images) of the aorta in order to support the assessment of individual aortic dissections and the differentiation between the true lumen and the false lumen.

In one or more embodiments, the AD strain analysis procedure 390 performs analysis of the strain map for the aortic wall and dissection flap at each phase of the cardiac cycle to provide information on the mobility of the dissection flap and to identify pressurization of the false lumen and compression of the true lumen over the cardiac cycle to support clinical assessment for diagnostic and disease management purposes.

In one or more embodiments, the AD strain analysis procedure 390 performs analysis of the strain map for the dissection flap at each phase of the cardiac cycle to identify regional weakening at the region near the tear(s) and at the tear margins with the potential to predict the evolution of the tear and its enlargement that will promote increased false lumen flow and patency, therefore supporting clinical assessment and diagnosis of individual dissections.

In one or more embodiments, the AD strain analysis procedure 30 performs analysis of the strain map for the aortic wall and dissection flap over the cardiac cycle at one or more follow-up scans with respect to a baseline scan in order to assess the temporal evolution of the strain and identify rapid changes in local strain as indicative of a rapid degenerative and weakening process likely to adversely affect disease progression, therefore supporting clinical assessment and diagnosis of individual dissections.

The AD strain mapping procedure 300 enables visualizing and assessing the mutual interaction between the flow channels (e.g., true and false lumen) created by the dissection flap, such as presence of blood in the false lumen that pressurizes the false lumen and compresses the true lumen over a cardiac cycle, and which may lead to complications due to the blood supply to downstream organs being limited. The AD strain mapping procedure 300 enables using strains to locate and identify tear points in the dissected blood vessel, which may be used to predict further tears, as well as understanding interactions between the true lumen and the false lumen in the dissected blood vessel.

It will be appreciated that the AD strain mapping procedure 300 does not require using shear stress calculations, thickness calculations, and computational fluid dynamics (CFD) or fluid-structure interaction (FSI) simulation with assumption of homogenous material properties of the aorta, and thus provides a more efficient and realistic assessment of strains in a dissected blood vessel.

In one embodiment, computational fluid dynamic (CFD) simulations may be used in conjunction with the strain maps in order to estimate blood flow in the true lumen and false lumen, when clear false lumen flow is identified, and provide complementary information on the blood perfusion to organs downstream of the dissection.

Method Description

Figure 6:
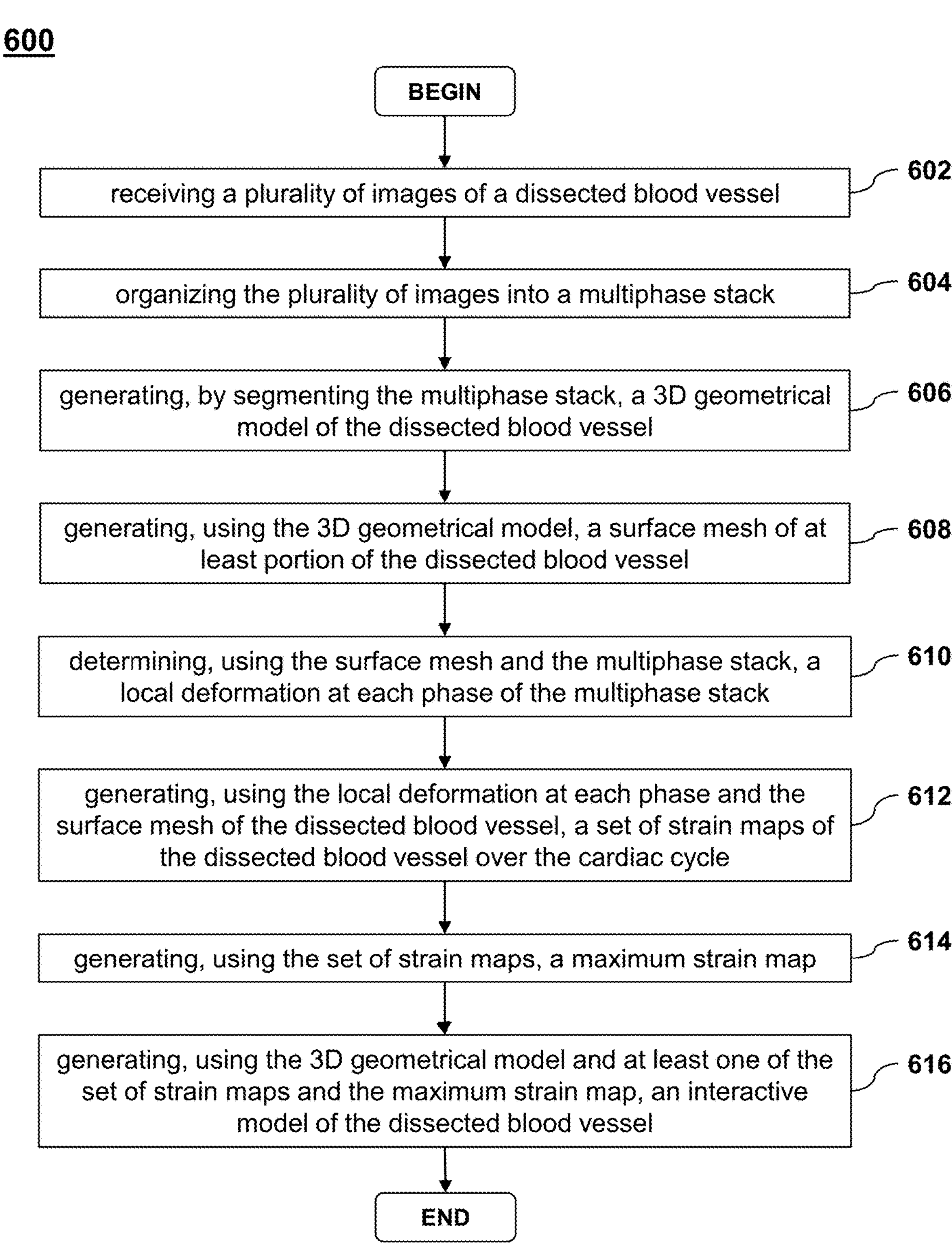
FIG. 6 depicts a flow chart of a method for in vivo strain mapping of a dissected blood vessel, the method being executable in accordance with non-limiting embodiments of the present technology.

FIG. 6 depicts a flowchart of a method 600 of generating a strain map of a dissected blood vessel, the method 600 being executable in accordance one or more non-limiting embodiments of the present technology.

The method 600 is executed by a processing device. For example, the method 600 may be executed by the server 230 or by the workstation computer 215. In one embodiment, the server 230 comprises a processor 110 and/or the GPU 111 operatively connected to a non-transitory storage medium such as the solid-state drive 120 and/or the random-access memory 130 storing computer-readable instructions. The processing device, upon executing the computer-readable instructions, is configured to execute the method 600.

It should be noted that the method 600 may be executed by more than one electronic device.

The method 600 begins at processing step 602.

At processing step 602, the processing device receives a plurality of images of the blood vessel of a given subject during a cardiac cycle having been acquired by using an ECG-gated medical imaging apparatus such as the medical imaging apparatus 210.

In one or more other embodiments, the plurality of images are received from at least one of the workstation computer 215, the database 235 and the medical imaging apparatus 210.

At processing step 604, the processing device organizes the plurality of images into a multiphase stack. In one or more embodiments, the workstation computer 215 may organize the plurality of images into the multiphase stack and transmit the multiphase stack to the server 230. A given phase of the multiphase stack is representative of the dissected blood vessel at a given time in a cardiac cycle.

At processing step 606, the processing device generates a 3D geometrical model of the dissected blood vessel by segmenting the multiphase stack. The 3D geometrical model comprises a wall of the dissected blood vessel and the dissection flap. The processing device generates the 3D geometrical based on the first phase of the multiphase stack, corresponding to a time in the cardiac cycle identified as phase 0.

In one or more embodiments, the processing device performs segmentation of the plurality of images and/or the multiphase stack by using one or more machine learning model to obtain the 3D geometrical model of the dissected blood vessel, which comprises the true lumen and false lumen defined by the dissection flap. In one or more other embodiments, the processing device receives an indication of the dissection flap and the aortic wall in order to generate the 3D geometrical model of the dissected blood vessel.

At processing step 608, the processing device generates, using the 3D geometrical model, a surface mesh of the at least portion of the dissected blood vessel for a first phase of the multiphase stack, the surface mesh comprising a wall surface mesh and a dissection flap surface mesh.

In one or more embodiments, the surface mesh of the dissected blood vessel comprises a surface mesh of the true lumen and a surface mesh of the false lumen of the dissected blood vessel.

In one or more embodiments, processing device smooths and meshes the 3D geometrical model of the dissected blood vessel to obtain a surface mesh of the 3D geometrical model of the dissected blood vessel. In one embodiment, the surface mesh of the 3D geometrical model of the dissected blood vessel is in the form of discretized geometry of small triangular elements.

At processing step 610, the processing device determines, using the surface mesh of the at least portion of the dissected blood vessel and the multiphase stack, a local deformation at each phase of the multiphase stack by mapping voxels of the surface mesh to the multiphase stack.

In one or more embodiments, the processing device maps each voxel position of the surface mesh for the first phase to all the subsequent phases. The position of all the voxels at the different phases is mapped back to the surface mesh for the first phase, where each node position of the geometry at the first phase is associated with node positions corresponding to all the subsequent phases. The processing device determines the nodal displacement throughout the cardiac cycle, i.e., different phases. The processing device then determines, using the nodal displacements throughout the cardiac cycle, the local deformation at each phase of the multiphase stack, i.e., different times during the cardiac cycle. The local deformation is indicative of nodal displacements and enables monitoring the position of portions of the surface of the true and false lumens when blood flows in the dissected blood vessel during the cardiac cycle of the given patient.

The method 600 advances to processing step 612.

At processing step 612, the processing device generates, using the local deformation at each phase and the surface mesh of the blood vessel wall and the surface mesh of the dissection flap, a set of strain maps, a given strain map of the set of strain maps including principal strain values at the surface mesh of the blood vessel wall and at the surface mesh the dissection flap for a given phase of the cardiac cycle. The set of strain maps includes at least one strain map for a given phase of the cardiac cycle. In one or more embodiments, the strain map comprises axial strain values and circumferential strain values of the dissected blood vessel.

In one or more embodiments, the set of strain maps includes a strain map for each phase of the cardiac cycle.

In one or more embodiments, the method 600 advances to processing step 616. In one or more alternative embodiments, the method 600 may end at processing step 612.

At processing step 614, the processing device generates, based on the set of strain maps, a maximum strain map indicative of maximum principal strain values at the surface mesh of the blood vessel wall and at the surface mesh the dissection flap over the cardiac cycle. The processing device determines the maximal principal strain values as the maximum of the three principal strain values at each phase of the cardiac cycle to obtain the maximum principal strain map over the cardiac cycle for the surface mesh of the blood vessel wall and the dissection flap.

In one or more embodiments, the method 600 advances to step 616. In one or more alternative embodiments, the method 600 may end at processing step 614.

At processing step 616, the processing device generates, using the 3D geometrical model and at least one of the sets of strain maps and the maximum strain map, an interactive model of the dissected blood vessel.

In one or more embodiments, the processing device transmits the interactive model of the dissected blood vessel for display. In one or more embodiments, the processing device transmits the interactive model of the dissected blood vessel for display on a display screen, such as the display interface 140 and/or the input/output interface 150.

The method 600 then ends.

Processing steps 602-616 may be repeated for the given patient at different times to assess the evolution of the dissected blood vessel. In one or more embodiments, the processing device uses the strain maps to predict a regional weakening in the dissected blood vessel. Additionally or alternatively, the processing device predicts, using the strain maps, an enlargement of the dissection tear(s) in the dissected blood vessel.

It should be expressly understood that not all technical effects mentioned herein need to be enjoyed in each and every embodiment of the present technology. For example, embodiments of the present technology may be implemented without the user enjoying some of these technical effects, while other non-limiting embodiments may be implemented with the user enjoying other technical effects or none at all.

Some of these steps and signal sending-receiving are well known in the art and, as such, have been omitted in certain portions of this description for the sake of simplicity. The signals can be sent-received using optical means (such as a fiber-optic connection), electronic means (such as using wired or wireless connection), and mechanical means (such as pressure-based, temperature based or any other suitable physical parameter based).

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

What is claimed is:

1. A method for generating a strain map of a dissected blood vessel of a given subject, the method being executed by a processor, the method comprising:

receiving a multiphase stack having been generated from a plurality of images of the dissected blood vessel of the given subject, each one of phases of the multiphase stack being representative of the dissected blood vessel at a respective time in a cardiac cycle;

generating, using at least a portion of the multiphase stack, a 3D geometrical model of at least a portion of the dissected blood vessel, the 3D geometrical model comprising a wall of the dissected blood vessel and a dissection flap;

generating, using the 3D geometrical model, a surface mesh of at least the portion of the dissected blood vessel for a given one of the phases of the multiphase stack, the surface mesh of at least the portion of the dissected blood vessel comprising a blood vessel wall surface mesh and a dissection flap surface mesh;

determining, using the surface mesh of at least the portion of the dissected blood vessel and the multiphase stack, a local deformation at each phase of the multiphase stack by mapping each node of the surface mesh of the dissected blood vessel to a respective voxel of each one of the phases of the multiphase stack;

generating, using the local deformation at each one of the phases and the blood vessel wall surface mesh and the dissection flap surface mesh, a set of strain maps, a given strain map of the set of strain maps including principal strain values at the surface of the dissected blood vessel for a corresponding phase of the cardiac cycle; and outputting the set of strain maps.

2. The method of claim 1, wherein said generating the set of strain maps comprises, for the given strain map, projecting strain in principal directions of curvature to obtain a circumferential strain value and an axial strain value on the surface mesh of the dissected blood vessel.

3. The method of claim 1, wherein said generating using the multiphase stack, the 3D geometrical model of at least the portion of the dissected blood vessel comprises:

segmenting the multiphase stack to obtain a segmented dissected blood vessel and using the segmented dissected blood vessel to obtain the 3D geometrical model.

4. The method of claim 1, wherein said mapping each node of the surface mesh to the respective voxel of each one of the phases of the multiphase stack is performed using an optical flow algorithm.

5. The method of claim 1, wherein the 3D geometrical model of at least the portion of the dissected blood vessel comprises an indication of a true lumen and a false lumen.

6. The method of claim 5, further comprising:

assessing, using the set of strain maps of the dissected blood vessel, a mobility of the dissection flap; and identifying pressurization of the false lumen and compression of the true lumen over the cardiac cycle.

7. The method of claim 1, wherein the 3D geometrical model of at least a portion of the dissected blood vessel further comprises an indication of a healthy non-dissected region of the blood vessel, the method further comprising determining, using the set of strain maps of the dissected blood vessel over the cardiac cycle and the indication of the healthy non-dissected region, a regional weakening in the dissected blood vessel.

8. The method of claim 1, further comprising:

predicting, using the set of strain maps of the dissection flap, an enlargement of a dissection tear in the dissected blood vessel.

9. The method of claim 1, further comprising:

repeating said method for a second multiphase stack of the dissected blood vessel of the given subject having been acquired at a subsequent time to thereby obtain a further 3D geometrical model of the dissected blood vessel and a further set of strain maps for the subsequent time.

10. The method of claim 9, further comprising:

predicting, using the set of strain maps and the further set of strain maps, at least one of a further regional weakening in the dissected blood vessel and a further enlargement of a dissection tear in the dissected blood vessel.

11. A system comprising:

a processor; and a non-transitory storage medium operatively connected to the processor, the non-transitory storage medium comprising computer-readable instructions stored thereon;

the processor, upon executing the computer-readable instructions, being configured for:

receiving a multiphase stack having been generated from a plurality of images of the dissected blood vessel of the given subject, each one of phases of the multiphase stack being representative of the dissected blood vessel at a respective time in a cardiac cycle;

generating, using at least a portion of the multiphase stack, a 3D geometrical model of at least a portion of the dissected blood vessel, the 3D geometrical model comprising a wall of the dissected blood vessel and a dissection flap;

generating, using the 3D geometrical model, a surface mesh of at least the portion of the dissected blood vessel for a given one of the phases of the multiphase stack, the surface mesh of at least the portion of the dissected blood vessel comprising a blood vessel wall surface mesh and a dissection flap surface mesh;

determining, using the surface mesh of at least the portion of the dissected blood vessel and the multiphase stack, a local deformation at each phase of the multiphase stack by mapping each node of the surface mesh of the dissected blood vessel to a respective voxel of each one of the phases of the multiphase stack;

generating, using the local deformation at each one of the phases and the blood vessel wall surface mesh and the dissection flap surface mesh, a set of strain maps, a given strain map of the set of strain maps including principal strain values at the surface of the dissected blood vessel for a corresponding phase of the cardiac cycle; and outputting the set of strain maps.

12. The system of claim 11, wherein said generating the set of strain maps comprises, for the given strain map, projecting strain in principal directions of curvature to obtain a circumferential strain value and an axial strain value on the surface mesh of the dissected blood vessel.

13. The system of claim 11, wherein said generating using the multiphase stack, the 3D geometrical model of at least the portion of the dissected blood vessel comprises:

segmenting the multiphase stack to obtain a segmented dissected blood vessel and using the segmented dissected blood vessel to obtain the 3D geometrical model.

14. The system of claim 11, wherein said mapping each node of the surface mesh to the respective voxel of each one of the phases of the multiphase stack is performed using an optical flow algorithm.

15. The system of claim 11, wherein the 3D geometrical model of at least the portion of the dissected blood vessel comprises an indication of a true lumen and a false lumen.

16. The system of claim 15, wherein the processor is further configured for:

assessing, using the set of strain maps of the dissected blood vessel, a mobility of the dissection flap; and identifying pressurization of the false lumen and compression of the true lumen over the cardiac cycle.

17. The system of claim 11, wherein the 3D geometrical model of at least a portion of the dissected blood vessel further comprises an indication of a healthy non-dissected region of the blood vessel, the processor being further configured for determining, using the set of strain maps of the dissected blood vessel over the cardiac cycle and the indication of the healthy non-dissected region, a regional weakening in the dissected blood vessel.

18. The system of claim 11, wherein the processor is further configured for:

predicting, using the set of strain maps, an enlargement of a dissection tear in the dissected blood vessel.

19. The system of claim 11, wherein the processor is further configured for executing the computer-readable instructions for a second multiphase stack of the dissected blood vessel of the given subject having been acquired at a subsequent time to thereby obtain a further 3D geometrical model of the dissected blood vessel and a further strain map for the subsequent time.

20. The system of claim 19, wherein the processor is further configured for:

predicting, using the set of strain maps and the further set of strain maps, at least one of a further regional weakening in the dissected blood vessel and a further enlargement of a dissection tear in the dissected blood vessel.

* * * * *